US00PP32585P2

(12) United States Plant Patent
Burton

(10) Patent No.: US PP32,585 P2
(45) Date of Patent: Dec. 8, 2020

(54) ***HEBE* PLANT NAMED 'HEBANN05'**

(50) Latin Name: *Hebe speciosa*
Varietal Denomination: HEBANN05

(71) Applicant: Steve Burton, Tamahere (NZ)

(72) Inventor: Steve Burton, Tamahere (NZ)

( * ) Notice: Subject to any disclaimer, the term of this patent is extended or adjusted under 35 U.S.C. 154(b) by 0 days.

(21) Appl. No.: 16/873,319

(22) Filed: Mar. 17, 2020

(51) Int. Cl.
*A01H 6/68* (2018.01)
*A01H 5/02* (2018.01)

(52) U.S. Cl.
USPC ..... Plt./251

(58) Field of Classification Search
USPC ..... Plt./251, 263.1, 226
See application file for complete search history.

*Primary Examiner* — Annette H Para
(74) *Attorney, Agent, or Firm* — Cassandra Bright

(57) ABSTRACT

A new and distinct cultivar of *Hebe* plant named 'HEBANN05' is disclosed, characterized by green-grey foliage with magenta tips. Plants produce racemes with trumpet shaped florets colored cerise. The new cultivar is a *Hebe*, suitable for ornamental garden purposes.

2 Drawing Sheets

Figure 1:
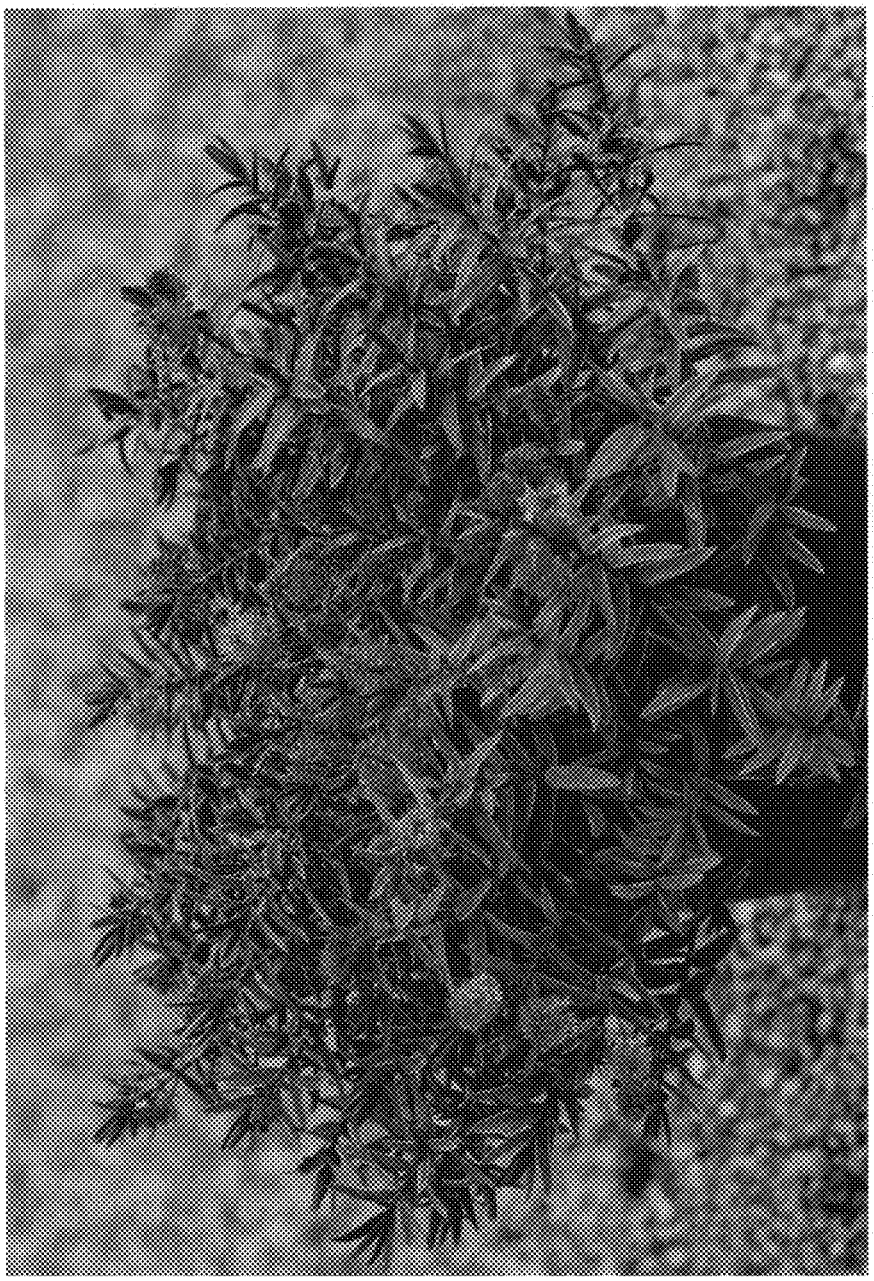

Latin name of the genus and species: *Hebe speciosa.*
Variety denomination: 'HEBANN05'.

BACKGROUND OF THE INVENTION

The new cultivar is a product of chance discovery by the inventor. This new variety, hereinafter referred to as 'HEBANN05', was discovered as a naturally occurring single branch mutation of *Hebe* 'Marilyn Monroe', unpatented. The discovery and selection of the new variety was made in 2015 at a commercial nursery in Cambridge, New Zealand.

After identifying the new variety as a potentially interesting selection, the inventor first organized propagation of 'HEBANN05' by vegetative terminal cuttings in 2015 at the same commercial nursery in Cambridge, New Zealand. The inventor continued controlled testing and propagation, assessing stability of the unique characteristics of this variety. At least three generations have been reproduced and have shown that the unique features of this cultivar are stable and reproduced true to type. Date of first sale was Mar. 20, 2019, occurring in Australia. This sale was made directly by the inventor or one who obtained the claimed invention directly or indirectly from the inventor. This sale and all public disclosures made between Mar. 20, 2019 and the filing of this application fall within the exception allowed under 102(b)(1).

SUMMARY OF THE INVENTION

The cultivar 'HEBANN05' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HEBANN05' These characteristics in combination distinguish 'HEBANN05' as a new and distinct *Hebe* cultivar:

1. Green-grey foliage with magenta tips.
2. Cerise-colored blooms in Summer.

COMPARISON TO PARENT VARIETY

'HEBANN05' is similar in most horticultural characteristics to the parent *Hebe* 'Marilyn Monroe'. Plants of the new cultivar 'HEBANN05' however differ in the following:

1. The new variety has green-grey foliage, while the parent has green foliage.
2. The new variety is a wider plant than the seed parent.

COMMERCIAL COMPARISON

'HEBANN05' can be compared to the unpatented commercial variety *Hebe* 'Annie's Winter Wonder'. Plants of the new cultivar 'HEBANN05' are similar to plants of 'Annie's Winter Wonder' in most horticultural characteristics, however, plants of the new cultivar 'HEBANN05' differ in the following:

1. Foliage of the new variety has non-variegated green-grey foliage; foliage of this comparator has green and cream variegation.

'HEBANN05' can be compared to the unpatented commercial variety *Hebe* 'Pretty n Pink'. Plants of the new cultivar 'HEBANN05' are similar to plants of 'Pretty n Pink' in some horticultural characteristics, however, plants of the new cultivar 'HEBANN05' differ in the following;

1. Foliage of the new variety is green-grey, while foliage of this comparator is deep green.
2. The new variety is a taller plant than this comparator.

BRIEF DESCRIPTION OF THE PHOTOGRAPHS

The accompanying photograph in FIG. 1 illustrates in full color a typical plant of 'HebAnn05', in a 1 gallon pot at approximately 18 months of age.

Figure 2:
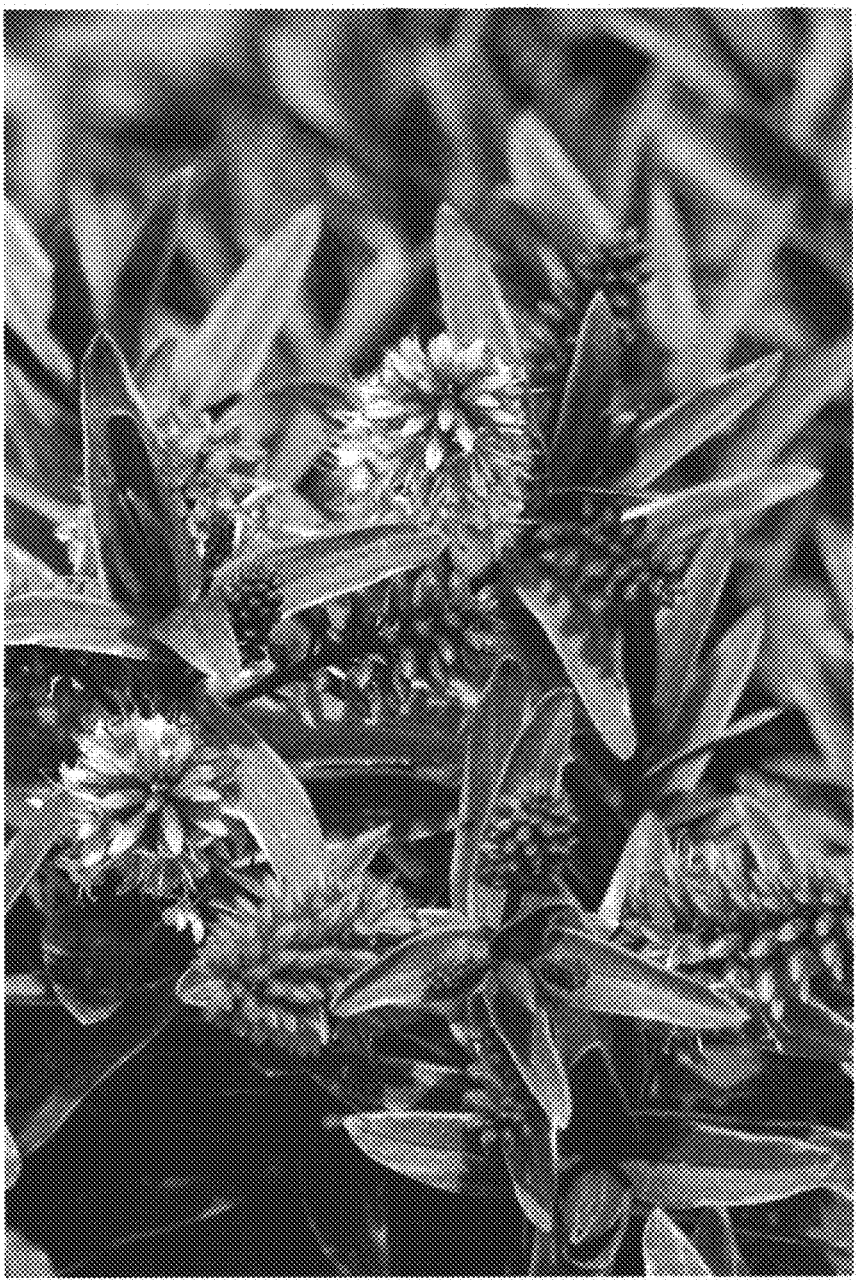

FIG. 2 illustrates in full color a close up view of foliage of the new variety.

The photographs were taken using conventional techniques and although colors may appear different from actual colors due to light reflectance they are as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HEBANN05' plants grown outdoors in Cambridge, New Zealand. Plants are approximately 2 years old, in a 3 gallon nursery container. Measurements and numerical values represent averages of typical plant types.
Botanical classification: *Hebe* x *speciosa* 'HEBANN05'.

PROPAGATION

Rooting: Approximately 1 month at 18° C. to initiate rooting. Approximately 3 months 18° C. to produce a rooted cutting.
Root description: Fine, fibrous young roots, well branched. Colored near RHS Grey-Brown 199A.

PLANT

Growth habit: Medium mounded habit.
Growth rate: Moderate.
Height: 50 cm.
Plant spread: 70 cm.
Age of plant described: 2 years.

FOLIAGE

Leaf:
- *Type*.—Simple.
- *Arrangement*.—Opposite decussate pairs.
- *Average length*.—40 mm.
- *Average width*.—10 mm.
- *Shape of blade*.—Elliptic.
- *Apex*.—Broad acute.
- *Base*.—Truncate.
- *Attachment*.—Sessile.
- *Margin*.—Entire.
- *Texture of top surface*.—Glabrous.
- *Texture of bottom surface*.—Glabrous.
- *Color*.—Young foliage upper side: Near RHS Greyed-Green 191A flushed Greyed-Purple 187D and 186A. Thin margin near Greyed-Green 193D. Young foliage under side: Near RHS Greyed-Green 191A flushed Greyed-Purple 187D and 186A. Thin margin near Greyed-Green 193D. Mature foliage upper side: Near RHS Greyed-Green 191A. Thin margin near Greyed-Green 193D. Mature foliage under side: Near RHS Greyed-Green 191A. Thin margin near Greyed-Green 193D.
- *Venation*.—Indistinguishable from leaf blade.

FLOWER

Bloom period: Summer until Autumn.
Flower: Raceme, tapered with trumpet shaped florets.
Inflorescence:
- *Height*.—50 mm.
- *Diameter*.—20 to 30 mm.
- *Type*.—Raceme.
- *Quantity*.—2 to 5 at upper axils.

Individual flowers:
- *Length*.—5 mm.
- *Diameter*.—5 mm.
- *Quantity*.—Average 20-40 florets per inflorescence.
- *Shape*.—Trumpet.

Petals:
- *Quantity*.—4.
- *Length*.—3 mm.
- *Width*.—*Approximately* 1-2 mm.
- *Apex*.—Rounded.
- *Base*.—Fused.
- *Shape of petal*.—Oblong.
- *Petal margin*.—Entire.
- *Petal arrangement*.—Rotate, base fused.
- *Petal texture*.—Smooth, glabrous all surfaces.
- *Color*.—Outside: RHS Red-Purple 70B. Inside: RHS Purple N80B.

Pedicle:
- *Length*.—3-4 mm.
- *Diameter*.—2 mm.
- *Color*.—Near RHS Greyed-Green 197A.
- *Texture*.—Glabrous.
- *Aspect*.—Straight.
- *Strength*.—Moderately sturdy.

Bud:
- *Shape*.—Ovate.
- *Length*.—1 mm.
- *Diameter*.—1 mm.
- *Color*.—RHS Purple N79B.

Sepals:
- *Quantity per flower*.—4 or 5.
- *Shape*.—Ovate.
- *Length*.—1 mm.
- *Width*.—1 mm.
- *Apex*.—Acute.
- *Base*.—Fused.
- *Margin*.—Entire.
- *Texture*.—Glabrous.
- *Color*.—Inner Surface: Near RHS Greyed-Green 195A. Outer Surface: Near RHS Greyed-Green 195A.

Fragrance: None.

REPRODUCTIVE ORGANS

Stamens:
- *Number*.—2.
- *Filament*.—Length: 9 mm. Color: RHS Purple-Red 186C.
- *Anthers*.—Length: Approximately 1 mm. Shape: Heart. Color: RHS Purple-Red 71A. Pollen: Quantity: Moderate. Color: RHS Yellow 18B.

Pistil:
- *Number*.—1.
- *Length*.—8 mm.
- *Color*.—RHS Purple N77B.
- *Style*.—Length: 5 mm. Color: RHS Purple N77B.

OTHER CHARACTERISTICS

Disease and pest resistance: Moderate resistance to normal diseases and pests of *Hebe*. Mildew during wet periods.
Temperature tolerance: Cold hardy to −3° C. Ideal growing temperature 10-28° C.
Fruit/seed production: Not observed to date.

What is claimed is:

1. A new and distinct cultivar of *Hebe* plant named 'HEBANN05' as herein illustrated and described.

* * * * *